United States Patent
Mazar et al.

(10) Patent No.: US 8,054,178 B2
(45) Date of Patent: *Nov. 8, 2011

(54) SYSTEM AND METHOD FOR CORRELATING BIOMETRIC TRENDS WITH A RELATED TEMPORAL EVENT

(75) Inventors: Scott T. Mazar, Woodbury, MN (US); Bruce H. KenKnight, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 105 days.

This patent is subject to a terminal disclaimer.

(21) Appl. No.: 12/476,833

(22) Filed: Jun. 2, 2009

(65) Prior Publication Data

US 2009/0273468 A1 Nov. 5, 2009

Related U.S. Application Data

(63) Continuation of application No. 11/869,611, filed on Oct. 9, 2007, now Pat. No. 7,554,438, which is a continuation of application No. 10/335,396, filed on Jan. 3, 2003, now Pat. No. 7,378,955.

(51) Int. Cl.
*G08B 1/08* (2006.01)
*G08B 1/00* (2006.01)
*A61B 5/00* (2006.01)
*A61N 1/00* (2006.01)

(52) U.S. Cl. .......... 340/539.12; 600/300; 600/301; 607/60; 340/531

(58) Field of Classification Search .......... 340/539.12; 600/300, 301
See application file for complete search history.

(56) References Cited

U.S. PATENT DOCUMENTS

| 4,310,003 | A | 1/1982 | Schlager |
| 4,519,395 | A | 5/1985 | Hrushesky |
| 4,777,960 | A | 10/1988 | Berger et al. |
| 4,796,634 | A | 1/1989 | Huntsman et al. |
| 4,838,275 | A | 6/1989 | Lee |
| 4,967,749 | A | 11/1990 | Cohen |
| 5,031,629 | A | 7/1991 | DeMarzo |
| 5,047,930 | A | 9/1991 | Martens et al. |
| 5,306,293 | A | 4/1994 | Zacouto |
| 5,330,505 | A | 7/1994 | Cohen |
| 5,554,177 | A | 9/1996 | Kieval et al. |

(Continued)

FOREIGN PATENT DOCUMENTS

EP 0297675 A1 1/1989

(Continued)

OTHER PUBLICATIONS

"U.S. Appl. No. 10/323,590, Amendment and Response filed Oct. 29, 2007 to Final Office Action mailed Aug. 6, 2007", 19 pgs.

(Continued)

*Primary Examiner* — George A Bugg
*Assistant Examiner* — Jack Wang
(74) *Attorney, Agent, or Firm* — Schwegman, Lundberg & Woessner, P.A.

(57) ABSTRACT

Systems and methods for correlating biometric trends with a related temporal event are disclosed. A preferred embodiment utilizes an implantable medical device comprising at least one sensor in electronic communication with a patient management system adapted to temporally analyze and correlate biometric data. Some embodiments of a system disclosed herein also can be configured as an Advanced Patient Management system that helps better monitor, predict and manage chronic diseases.

19 Claims, 3 Drawing Sheets

U.S. PATENT DOCUMENTS

| | | | |
|---|---|---|---|
| 5,626,630 A | 5/1997 | Markowitz et al. | |
| 5,674,256 A | 10/1997 | Carlson | |
| 5,697,959 A | 12/1997 | Poore | |
| 5,700,283 A | 12/1997 | Salo | |
| 5,722,999 A | 3/1998 | Snell | |
| 5,724,985 A | 3/1998 | Snell et al. | |
| 5,731,296 A | 3/1998 | Sollevi | |
| 5,732,709 A | 3/1998 | Tacklind et al. | |
| 5,759,199 A | 6/1998 | Snell et al. | |
| 5,790,534 A | 8/1998 | Kokko et al. | |
| 5,792,064 A | 8/1998 | Panescu et al. | |
| 5,822,544 A | 10/1998 | Chaco et al. | |
| 5,836,987 A | 11/1998 | Baumann et al. | |
| 5,860,918 A | 1/1999 | Schradi et al. | |
| 5,904,708 A | 5/1999 | Goedeke | |
| 5,935,078 A | 8/1999 | Feierbach | |
| 5,935,081 A | 8/1999 | Kadhiresan | |
| 5,942,986 A | 8/1999 | Shabot et al. | |
| 5,970,986 A | 10/1999 | Bolz et al. | |
| 6,015,388 A | 1/2000 | Sackner et al. | |
| 6,024,089 A | 2/2000 | Wallace et al. | |
| 6,024,699 A | 2/2000 | Surwit et al. | |
| 6,044,298 A | 3/2000 | Salo et al. | |
| 6,045,513 A | 4/2000 | Stone et al. | |
| 6,058,329 A | 5/2000 | Salo et al. | |
| 6,073,048 A | 6/2000 | Kieval et al. | |
| 6,076,015 A | 6/2000 | Hartley et al. | |
| 6,093,146 A | 7/2000 | Filangeri | |
| 6,110,522 A | 8/2000 | Lepper et al. | |
| 6,115,630 A | 9/2000 | Stadler et al. | |
| 6,144,880 A | 11/2000 | Ding et al. | |
| 6,190,324 B1 | 2/2001 | Kieval et al. | |
| 6,206,829 B1 | 3/2001 | Iliff | |
| 6,275,727 B1 | 8/2001 | Hopper et al. | |
| 6,280,409 B1 | 8/2001 | Stone et al. | |
| 6,336,900 B1 | 1/2002 | Alleckson et al. | |
| 6,351,673 B1 | 2/2002 | Ding et al. | |
| 6,360,127 B1 | 3/2002 | Ding et al. | |
| 6,383,136 B1 | 5/2002 | Jordan | |
| 6,416,471 B1 | 7/2002 | Kumar et al. | |
| 6,434,429 B1 | 8/2002 | Kraus et al. | |
| 6,438,407 B1 | 8/2002 | Ousdigian et al. | |
| 6,441,747 B1 | 8/2002 | Khair et al. | |
| 6,470,215 B1 | 10/2002 | Kraus et al. | |
| 6,490,487 B1 | 12/2002 | Kraus et al. | |
| 6,514,195 B1 | 2/2003 | Ferek-Petric | |
| 6,542,775 B2 | 4/2003 | Ding et al. | |
| 6,592,528 B2 | 7/2003 | Amano | |
| 6,602,191 B2 | 8/2003 | Quy | |
| 6,628,989 B1 | 9/2003 | Penner et al. | |
| 6,643,548 B1 | 11/2003 | Mai et al. | |
| 6,665,558 B2 | 12/2003 | Kalgren et al. | |
| 6,684,103 B2 | 1/2004 | Ding et al. | |
| 6,735,479 B2 | 5/2004 | Fabian et al. | |
| 6,738,671 B2 | 5/2004 | Christophersom et al. | |
| 6,764,446 B2 | 7/2004 | Wolinsky et al. | |
| 6,816,744 B2 | 11/2004 | Garfield et al. | |
| 6,827,670 B1 | 12/2004 | Stark et al. | |
| 6,834,203 B2 | 12/2004 | Bardy | |
| 6,931,273 B2 | 8/2005 | Groenewegen et al. | |
| 6,937,899 B2 | 8/2005 | Sheldon et al. | |
| 6,944,495 B2 | 9/2005 | MacAdam et al. | |
| 6,961,617 B1 | 11/2005 | Snell | |
| 6,975,900 B2 | 12/2005 | Rudy et al. | |
| 7,024,248 B2 | 4/2006 | Penner et al. | |
| 7,043,305 B2 | 5/2006 | Kenknight et al. | |
| 7,047,065 B2 | 5/2006 | Kalgren et al. | |
| 7,060,031 B2 | 6/2006 | Webb et al. | |
| 7,115,096 B2 | 10/2006 | Siejko et al. | |
| 7,123,953 B2 | 10/2006 | Starobin et al. | |
| 7,136,707 B2 | 11/2006 | Hall et al. | |
| 7,209,786 B2 | 4/2007 | Brockway et al. | |
| 7,248,923 B2 | 7/2007 | Maile et al. | |
| 7,273,457 B2 | 9/2007 | Penner | |
| 7,378,955 B2* | 5/2008 | Mazar et al. | 340/539.12 |
| 7,429,243 B2* | 9/2008 | KenKnight et al. | 600/300 |
| 7,431,699 B2 | 10/2008 | Siejko et al. | |
| 7,468,032 B2 | 12/2008 | Stahmann et al. | |
| 7,480,528 B2 | 1/2009 | Brockway et al. | |
| 7,554,438 B2* | 6/2009 | Mazar et al. | 340/539.12 |
| 7,559,901 B2 | 7/2009 | Maile et al. | |
| 7,751,901 B2* | 7/2010 | Mazar et al. | 607/60 |
| 7,791,467 B2* | 9/2010 | Mazar et al. | 340/531 |
| 7,831,447 B2* | 11/2010 | Schuman | 705/2 |
| 7,837,629 B2* | 11/2010 | Bardy | 600/508 |
| 7,856,035 B2* | 12/2010 | Pierce et al. | 370/473 |
| 7,860,574 B2* | 12/2010 | Von Arx et al. | 607/60 |
| 7,959,568 B2 | 6/2011 | Stahmann et al. | |
| 7,983,745 B2 | 7/2011 | Hatlestad et al. | |
| 7,983,759 B2 | 7/2011 | Stahmann et al. | |
| 2001/0007053 A1 | 7/2001 | Bardy | |
| 2001/0031998 A1 | 10/2001 | Nelson et al. | |
| 2001/0039503 A1 | 11/2001 | Chan et al. | |
| 2001/0047125 A1 | 11/2001 | Quy | |
| 2001/0049471 A1 | 12/2001 | Suzuki et al. | |
| 2002/0019586 A1 | 2/2002 | Teller et al. | |
| 2002/0026103 A1 | 2/2002 | Norris et al. | |
| 2002/0026223 A1 | 2/2002 | Riff et al. | |
| 2002/0045808 A1 | 4/2002 | Ford et al. | |
| 2002/0049482 A1 | 4/2002 | Fabian et al. | |
| 2002/0103442 A1 | 8/2002 | Mulligan et al. | |
| 2002/0107641 A1 | 8/2002 | Schaeffer et al. | |
| 2002/0115939 A1 | 8/2002 | Mulligan et al. | |
| 2002/0156654 A1 | 10/2002 | Roe et al. | |
| 2002/0193670 A1 | 12/2002 | Garfield et al. | |
| 2003/0055679 A1 | 3/2003 | Soll et al. | |
| 2003/0088290 A1 | 5/2003 | Spinelli et al. | |
| 2003/0144702 A1 | 7/2003 | Yu et al. | |
| 2003/0144703 A1 | 7/2003 | Yu et al. | |
| 2003/0144711 A1 | 7/2003 | Pless et al. | |
| 2003/0171791 A1 | 9/2003 | KenKnight et al. | |
| 2003/0233031 A1 | 12/2003 | Rice | |
| 2003/0235816 A1 | 12/2003 | Slawin et al. | |
| 2004/0019287 A1 | 1/2004 | White | |
| 2004/0073093 A1 | 4/2004 | Hatlestad | |
| 2004/0117204 A1 | 6/2004 | Mazar et al. | |
| 2004/0122294 A1 | 6/2004 | Hatlestad et al. | |
| 2004/0122295 A1 | 6/2004 | Hatlestad et al. | |
| 2004/0122296 A1 | 6/2004 | Hatlestad et al. | |
| 2004/0122297 A1 | 6/2004 | Stahmann et al. | |
| 2004/0122484 A1 | 6/2004 | Hatlestad et al. | |
| 2004/0122485 A1 | 6/2004 | Stahmann et al. | |
| 2004/0122486 A1 | 6/2004 | Stahmann et al. | |
| 2004/0122487 A1 | 6/2004 | Hatlestad et al. | |
| 2004/0133080 A1* | 7/2004 | Mazar et al. | 600/300 |
| 2005/0021370 A1 | 1/2005 | Riff et al. | |
| 2005/0042589 A1 | 2/2005 | Hatlestad et al. | |
| 2006/0195163 A1 | 8/2006 | KenKnight et al. | |
| 2006/0253300 A1 | 11/2006 | Somberg et al. | |
| 2008/0021287 A1 | 1/2008 | Woellenstein et al. | |
| 2008/0027757 A1 | 1/2008 | Mazar et al. | |
| 2009/0105554 A1 | 4/2009 | Stahmann et al. | |
| 2009/0124917 A1 | 5/2009 | Hatlestad et al. | |
| 2010/0063840 A1 | 3/2010 | Hoyme et al. | |

FOREIGN PATENT DOCUMENTS

| | | |
|---|---|---|
| EP | 0709058 A1 | 5/1996 |
| JP | 200167403 A2 | 3/2001 |
| JP | 2001299702 A2 | 10/2001 |
| JP | 2002514454 T | 5/2002 |
| JP | 2002183312 A2 | 6/2002 |
| JP | 2002311158 A2 | 10/2002 |
| WO | WO-9938278 A1 | 7/1999 |
| WO | WO-9958056 A1 | 11/1999 |
| WO | WO-9958086 A1 | 11/1999 |
| WO | WO-01/03575 A1 | 1/2001 |
| WO | WO-0124876 A1 | 4/2001 |
| WO | WO-0167948 A2 | 9/2001 |
| WO | WO-2004056266 A1 | 7/2004 |
| WO | WO-2004059551 A2 | 7/2004 |

OTHER PUBLICATIONS

"U.S. Appl. No. 10/323,590, Advisory Action mailed Nov. 16, 2006", 3 pgs.

"U.S. Appl. No. 10/323,590, Final Office Action mailed Aug. 6, 2007", 6 pgs.

"U.S. Appl. No. 10/323,590, Final Office Action mailed Sep. 5, 2006", 5 pgs.
"U.S. Appl. No. 10/323,590, Non Final Office Action mailed Jan. 19, 2006", 5 pgs.
"U.S. Appl. No. 10/323,590, Non Final Office Action mailed Feb. 20, 2007", 4 pgs.
"U.S. Appl. No. 10/323,590, Non Final Office Action mailed Jul. 21, 2005", 6 pgs.
"U.S. Appl. No. 10/323,590, Response filed May 21, 2007 to Non Final Office Action mailed Feb. 20, 2007", 17 pgs.
"U.S. Appl. No. 10/323,590, Response filed Jun. 19, 2006 to Non Final Office Action mailed Jan. 19, 2006", 16 pgs.
"U.S. Appl. No. 10/323,590, Response filed Oct. 24, 2006 to Final Office Action mailed Sep. 5, 2006", 17 pgs.
"U.S. Appl. No. 10/323,590, Response filed Nov. 2, 2005 to Non Final Office Action mailed Jul. 21, 2005", 12 pgs.
"U.S. Appl. No. 10/323,590, Non-Final Office Action mailed Jan. 9, 2008", 5 pgs.
"U.S. Appl. No. 10/323,590, Response filed Apr. 9, 2008 to Non-Final Office Action mailed Jan. 9, 2008", 19 pgs.
"U.S. Appl. No. 10/323,604, Amendment and Response filed Jan. 8, 2008 to Office Action mailed Aug. 8, 2007", 17 pgs.
"U.S. Appl. No. 10/323,604, Response filed Feb. 19, 2009 to Final Office Action mailed Aug. 19, 2008", 14 pgs.
"U.S. Appl. No. 10/323,604, Final Office Action mailed Aug. 19, 2008", 16 pgs.
"U.S. Appl. No. 10/323,604, Non-Final Office Action mailed Apr. 21, 2009", 20 pgs.
"U.S. Appl. No. 10/323,606, Examiner's Answer mailed Feb. 26, 2008", 29 pgs.
"U.S. Appl. No. 10/323,713, Non-Final Office Action mailed Sep. 28, 2007", 15 pgs.
"U.S. Appl. No. 10/323,713, Response filed Sep. 21, 2006 to Non Final Office Action mailed Jun. 21, 2006", 14 pgs.
"U.S. Appl. No. 10/323,713, Advisory Action mailed Jan. 31, 2007", 3 pgs.
"U.S. Appl. No. 10/323,713, Final Office Action mailed Nov. 8, 2006", 12 pgs.
"U.S. Appl. No. 10/323,713, Non-Final Office Action mailed Apr. 10, 2007", 13 pgs.
"U.S. Appl. No. 10/323,713, Non-Final Office Action mailed Jun. 21, 2006", 11 pgs.
"U.S. Appl. No. 10/323,713, Non-Final Office Action mailed Dec. 9, 2005", 10 pgs.
"U.S. Appl. No. 10/323,713, Response filed Jan. 8, 2007 to Final Office Action mailed Nov. 8, 2006", 17 pgs.
"U.S. Appl. No. 10/323,713, Response filed Mar. 26, 2007 to Final Office Action mailed Nov. 8, 2006", 15 pgs.
"U.S. Appl. No. 10/323,713, Response filed Apr. 18, 2006 to Non-Final Office Action mailed Dec. 9, 2005", 15 pgs.
"U.S. Appl. No. 10/323,713, Response filed Jul. 10, 2007 to Non Final Office Action mailed Apr. 10, 2007", 18 pgs.
"U.S. Appl. No. 10/323,713, Response filed Dec. 28, 2007 to Non-Final Office Action mailed Sep. 28, 2007", 19 pgs.
"U.S. Appl. No. 11/381,051, Preliminary Amendment filed May 1, 2006", 5 pgs.
"U.S. Appl. No. 11/381,051, Supplemental Preliminary Amendment filed Jul. 31, 2006", 6 pgs.
"U.S. Appl. No. 11/869,611, Notice of Allowance mailed Mar. 5, 2009", 7 pgs.
"U.S. Appl. No. 11/869,611, Response filed Jan. 27, 2009 to Non-Final Office Action mailed Dec. 23, 2008", 8 pgs.
"U.S. Appl. No. 11/869,611, Non-Final Office Action mailed Dec. 23, 2008", 6 pgs.
"Correlation", [online]. [retrieved Mar. 19, 2007]. Retrieved from the Internet: <URL: http://everything2.com/ index.pl?node=correlation>, (2001), 3 pgs.
"Prosecution File History for U.S. Appl. No. 10/093,353", (now US 7,043,305), 55 pgs.
"Prosecution File History for U.S. Appl. No. 10/323,604", 129 pgs.
"Prosecution File History for U.S. Appl. No. 10/323,606", 139 pgs.
"Prosecution File History for U.S. Appl. No. 10/323,860", 97 pgs.
"Prosecution File History for Application U.S. Appl. No. 10/335,396", 222 pgs.
Anderson, T. W., "R. A. Fisher and multivariate analysis", *Statist. Sci.*, 11(1), (1996), 20-34.
Garson, G. D., "Correlation", [on-line]. [retrieved Mar. 19, 2007]. Retrieved from the Internet: <URL: http://statisticssolutions.com/correlation.htm>, Statistics Solutions, Inc., (© 1998, 2006 by G. David Garson), 12 pgs.
Mazar, S. T., et al., "System and Method for Correlating Biometric Trends With a Related Temporal Event", U.S. Appl. No. 10/335,396, filed Jan. 3, 2003, 18 pgs.
Smith, R.A., et al., "An intranet database for pacemaker patients", *International Journal of Medicial Informatics*, 47, (1997), 79-82.
"U.S. Appl. No. 10/323,590, Final Office Action mailed Jul. 10, 2008", 9 pgs.
"U.S. Appl. No. 10/323,604, Appeal Brief filed Dec. 10, 2009", 54 pgs.
"U.S. Appl. No. 10/323,604, Decision on Pre-Appeal Brief Request mailed Nov. 10, 2009", 2 pgs.
"U.S. Appl. No. 10/323,604, Examiner's Answer to Appeal Brief mailed Sep. 6, 2010", 21 pgs.
"U.S. Appl. No. 10/323,604, Final Office Action mailed Feb. 12, 2007", 13 pgs.
"U.S. Appl. No. 10/323,604, Non-Final Office Action mailed Aug. 8, 2007", 13 pgs.
"U.S. Appl. No. 10/323,604, Non-Final Office Action mailed Dec. 30, 2005", 15 pgs.
"U.S. Appl. No. 10/323,604, Notice of Non-Compliant Brief mailed Jan. 11, 2010", 2 pgs.
"U.S. Appl. No. 10/323,604, Pre-Appeal Request filed Aug. 20, 2009", 5 pgs.
"U.S. Appl. No. 10/323,604, Reply Brief filed Oct. 5, 2010", 7 pgs.
"U.S. Appl. No. 10/323,604, Response filed Jan. 8, 2008 to Non-Final Office Action mailed Aug. 8, 2007", 17 pgs.
"U.S. Appl. No. 10/323,604, Response filed May 20, 2007 to Final Office Action mailed Feb. 12, 2007", 17 pgs.
"U.S. Appl. No. 10/323,604, Response filed Jun. 30, 2006 to Restriction Requirement mailed Dec. 30, 2005", 20 pgs.
"U.S. Appl. No. 10/323,604, Response filed Nov. 22, 2005 to Restriction Requirement mailed Oct. 26, 2005", 12 pgs.
"U.S. Appl. No. 10/323,604, Response to Notice of Non-Compliant Brief filed Feb. 11, 2010", 56 pgs.
"U.S. Appl. No. 10/323,604, Restriction Requirement mailed Oct. 26, 2005", 6 pgs.
"U.S. Appl. No. 10/323,604, Restriction Requirement mailed Dec. 9, 2005", 8 pgs.
"U.S. Appl. No. 10/323,606, Appeal Brief filed Aug. 6, 2007", 36 pgs.
"U.S. Appl. No. 10/323,606, Final Office Action mailed Apr. 5, 2007", 11 pgs.
"U.S. Appl. No. 10/323,606, Final Office Action mailed Dec. 19, 2006", 12 pgs.
"U.S. Appl. No. 10/323,606, Non-Final Office Action mailed Jan. 26, 2006", 35 pgs.
"U.S. Appl. No. 10/323,606, Notice of Allowance mailed Mar. 15, 2011", 7 pgs.
"U.S. Appl. No. 10/323,606, Notice of Allowance mailed Dec. 7, 2010", 6 pgs.
"U.S. Appl. No. 10/323,606, Reply Brief filed Apr. 28, 2008", 9 pgs.
"U.S. Appl. No. 10/323,606, Response filed Mar. 19, 2007 to Final Office Action mailed Dec. 19. 2006", 13 pgs.
"U.S. Appl. No. 10/323,606, Response filed May, 25, 2006 to Non Final Office Action mailed Jan. 26, 2006", 20 pgs.
"U.S. Appl. No. 10/323,606, Response filed Nov. 21, 2005 to Restriction Requirement mailed Oct. 28, 2005", 10 pgs.
"U.S. Appl. No. 10/323,606, Restriction Requirement mailed Oct. 28, 2006", 4 pgs.
"U.S. Appl. No. 10/323,616, Advisory Action mailed Feb. 28, 2010", 2 pgs.
"U.S. Appl. No. 10/323,616, Appeal Brief filed May 17, 2010", 43 pgs.
"U.S. Appl. No. 10/323,616, Examiner Interview Summary mailed Feb. 8, 2010", 3 pgs.

"U.S. Appl. No. 10/323,616, Examiner Interview Summary mailed Oct. 14, 2009", 3 pgs.

"U.S. Appl. No. 10/323,616, Examiner's Answer to Appeal Brief mailed Jul. 21, 2010", 27 pgs.

"U.S. Appl. No. 10/323,616, Final Office Action mailed Oct. 31, 2007", 17 pgs.

"U.S. Appl. No. 10/323,616, Final Office Action mailed Nov. 13, 2008", 19 pgs.

"U.S. Appl. No. 10/323,616, Final Office Action mailed Nov. 16, 2009", 26 pgs.

"U.S. Appl. No. 10/323,616, Non-Final Office Action mailed Mar. 19, 2008", 19 pgs.

"U.S. Appl. No. 10/323,616, Non-Final Office Action mailed Apr. 2, 2009", 22 pgs.

"U.S. Appl. No. 10/323,616, Non-Final Office Action mailed Apr. 20, 2007", 18 pgs.

"U.S. Appl. No. 10/323,616, Response filed Jan. 19, 2010 to Final Office Action mailed Nov. 16, 2009", 20 pgs.

"U.S. Appl. No. 10/323,616, Response filed Feb. 25, 2008 to Final Office Action mailed Oct. 31, 2007 ", 18 pgs.

"U.S. Appl. No. 10/323,616, Response filed Mar. 13, 2009 to Final Office Action mailed Nov. 13, 2008", 17 pgs.

"U.S. Appl. No. 10/323,616, Response filed Jul. 21, 2008 to Non-Final Office Action mailed Mar. 19, 2008", 12 pgs.

"U.S. Appl. No. 10/323,616, Response filed Aug. 3, 2009 to Non-Final Office Action mailed Apr. 2, 2009", 19 pgs.

"U.S. Appl. No. 10/323,616, Response filed Aug. 20, 2007 to Non-Final Office Action mailed Apr. 20, 2007", 37 pgs.

"U.S. Appl. No. 10/323,713, Final Office Action mailed Apr. 4, 2008", 16 pgs.

"U.S. Appl. No. 10/323,713, Notice of Allowance mailed Aug. 20, 2008", 9 pgs.

"U.S. Appl. No. 10/323,713, Preliminary Amendment mailed Dec. 17, 2003", 14 pgs.

"U.S. Appl. No. 10/323,713, Response filed Jul. 10, 2007 to Non-Final Office Action mailed Apr. 10, 2007", 18 pgs.

"U.S. Appl. No. 10/323,713, Response filed Jul. 30, 2008 to Final Office Action mailed Apr. 4, 2008", 11 pgs.

"U.S. Appl. No. 10/323,713, Response filed Oct. 10, 2005 to Restriction Requirement mailed Sep. 9, 2005", 11 pgs.

"U.S. Appl. No. 10/323,713, Restriction Requirement mailed Sep. 9, 2005", 6 pgs.

"U.S. Appl. No. 10/323,859, Decision on Pre-Appeal Brief Request mailed Jan. 14, 2010", 2 pgs.

"U.S. Appl. No. 10/323,859, Final Office Action mailed May 10, 2011", 20 pgs.

"U.S. Appl. No. 10/323,859, Final Office Action mailed Jun. 18, 2007", 8 pgs.

"U.S. Appl. No. 10/323,859, Final Office Action mailed Jul. 9, 2009", 9 pgs.

"U.S. Appl. No. 10/323,859, Non-Final Office Action mailed Mar. 29, 2006", 8 pgs.

"U.S. Appl. No. 10/323,859, Non-Final Office Action mailed Oct. 17, 2008", 7 pgs.

"U.S. Appl. No. 10/323,859, Non-Final Office Action mailed Nov. 26, 2010", 14 pgs.

"U.S. Appl. No. 10/323,859, Pre-Appeal Brief Request filed Dec. 9, 2009", 5 pgs.

"U.S. Appl. No. 10/323,859, Response filed Feb. 28, 2011 to Non-Final Office Action mailed Nov. 26, 2010", 19 pgs.

"U.S. Appl. No. 10/323,859, Response filed Mar. 17, 2009 to Non-Final Office Action mailed Oct. 17, 2008", 20 pgs.

"U.S. Appl. No. 10/323,859, Response filedJul. 11, 2011 to Final Office Action mailed May 10, 2011", 23 pgs.

"U.S. Appl. No. 10/323,859, Response filed Jun. 14, 2008 to Restriction Requirement mailed Jun. 12, 2008", 13 pgs.

"U.S. Appl. No. 10/323,859, Response filed Aug. 20, 2007 to Final Office Action mailed Jun. 18, 2007", 17 pgs.

"U.S. Appl. No. 10/323,859, Response filed Sep. 28, 2006 to Non Final office action mailed Mar. 29, 2006", 14 pgs.

"U.S. Appl. No. 10/323,859, Restriction Requirement mailed Jun. 12, 2008", 5 pgs.

"U.S. Appl. No. 10/323,859, Restriction Requirement mailed Jun. 12, 2008".

"U.S. Appl. No. 10/323,860, Advisory Action mailed Jun. 20, 2007", 4 pgs.

"U.S. Appl. No. 10/323,860, Advisory Action mailed Aug. 19, 2009", 3 pgs.

"U.S. Appl. No. 10/323,860, Appeal Brief filed Dec. 11, 2007", 33 pgs.

"U.S. Appl. No. 10/323,860, Decision on Pre-Appeal Brief Request mailed Aug. 1, 2007", 2 pgs.

"U.S. Appl. No. 10/323,860, Examiner Interview Summary mailed May 23, 2008", 2 pgs.

"U.S. Appl. No. 10/323,860, Examiner Interview Summary mailed Nov. 5, 2008", 2 pgs.

"U.S. Appl. No. 10/323,860, Final Office Action mailed Feb. 17, 2011", 7 pgs.

"U.S. Appl. No. 10/323,860, Final Office Action mailed Mar. 5, 2009", 12 pgs.

"U.S. Appl. No. 10/323,860, Final Office Action mailed Mar. 20, 2008", 11 pgs.

"U.S. Appl. No. 10/323,860, Final Office Action mailed Apr. 11, 2007", 9 pgs.

"U.S. Appl. No. 10/323,860, Final Office Action mailed Apr. 29, 2010", 11 pgs.

"U.S. Appl. No. 10/323,860, Non-Final Office Action mailed Mar. 2, 2006", 8 pgs.

"U.S. Appl. No. 10/323,860, Non-Final Office Action mailed Jul. 22, 2008", 11 pgs.

"U.S. Appl. No. 10/323,860, Non-Final Office Action mailed Aug. 4, 2010", 5 pgs.

"U.S. Appl. No. 10/323,860, Non-Final Office Action mailed Sep. 29, 2006", 12 pgs.

"U.S. Appl. No. 10/323,860, Non-Final Office Action mailed Oct. 28, 2009", 10 pgs.

"U.S. Appl. No. 10/323,860, Pre-Appeal Brief Request filed Jul. 11, 2007", 5 pgs.

"U.S. Appl. No. 10/323,860, Response filed Jan. 9, 2006 to Restriction Requirement mailed Dec. 7, 2005", 11 pgs.

"U.S. Appl. No. 10/323,860, Response filed Jan. 28, 2010 to Non Final Office Action mailed Oct. 28, 2009", 12 pgs.

"U.S. Appl. No. 10/323,860, Response filed Jan. 29, 2007 to Non-Final Office Action mailed Sep. 28, 2006", 15 pgs.

"U.S. Appl. No. 10/323,860, Response filed Jun. 2, 2006 to Non-Final Office Action mailed Mar. 2, 2006", 12 pgs.

"U.S. Appl. No. 10/323,860, Response filed Jun. 11, 2007 to Final Office Action mailed Apr. 11, 2007", 13 pgs.

"U.S. Appl. No. 10/323,860, Response filed Jun. 20, 2008 to Final Office Action mailed Mar. 20, 2008", 18 pgs.

"U.S. Appl. No. 10/323,860, Response filed Jun. 28, 2010 to Final Office Action mailed Apr. 29, 2010", 11 pgs.

"U.S. Appl. No. 10/323,860, Response filed Aug. 4, 2009 to Final Office Action mailed Mar. 5, 2009", 14 pgs.

"U.S. Appl. No. 10/323,860, Response filed Aug. 31, 2009 to Advisory Action mailed Aug. 19, 2009", 16 pgs.

"U.S. Appl. No. 10/323,860, Response filed Nov. 24, 2008 to Non Final Office Action mailed Jul, 22, 2008", 17 pgs.

"U.S. Appl. No. 10/323,860, Response filed Dec. 6, 2010 to Non Final Office Action mailed Aug. 4, 2010", 14 pgs.

"U.S. Appl. No. 10/323,860, Restriction Requirement mailed Dec. 7, 2005", 4 pgs.

"U.S. Appl. No. 10/335,396, Notice of Allowance mailed Nov. 30, 2007", 7 pgs.

"U.S. Appl. No. 10/335,396, Supplemental Notice of Allowability mailed Dec. 26, 2007", 5 pgs.

"U.S. Appl. No. 12/341,207, Notice of Allowance mailed Feb. 7, 2011", 10 pgs.

"U.S. Appl. No. 12/350,875, Notice of Allowance mailed Mar. 10, 2011", 5 pgs.

"European Application Serial No. 03813800.4, Office Action mailed Feb. 3, 2011", 6 pgs.

"European Application Serial No. 03814044.8, Communication mailed Apr. 21, 2008", 7 pgs.

"European Application Serial No. 03814044.8, Response filed Oct. 20, 2008 to Communication mailed Apr. 21, 2008", 14 pgs.

"International Application Serial No. PCT/US2003/040034, International Search Report mailed Apr. 4, 2005", 3 pgs.

"International Application Serial No. PCT/US2003/040662, International Search Report mailed May 28, 2004", 6 pgs.

"Japan Application Serial No. 2004-563613, Amendment filed Mar. 2, 2010 to Notice of Reasons for Rejection mailed Dec. 3, 2009", (w/ English Translation of Amended Claims), 11 pgs.

"Japan Application Serial No. 2004-563613, Notice of Reasons for Rejection mailed Dec. 3, 2009", (w/ English Translation), 7 pgs.

"Japanese Application Serial No. 2004-562326, Office Action mailed Feb. 3, 2010", (w/ English Translation), 7 pgs.

"Japanese Application Serial No. 2004-562326, Office Action mailed Feb. 24, 2011", 3 pgs.

"Japanese Application U.S. Serial No. 2004-562326, Response filed May 2, 2011 to Non-Final Office Action mailed Feb. 7, 2011", 5 pgs.

"Japanese Application Serial No. 2004-562326, Response filed Aug. 2, 2010 to Office Action dated Feb. 3, 2010", (w/ English Translation of Amended Claims), 13 pgs.

"Japanese Application Serial No. 2004-563613, Notice of Allowance mailed May 20, 2011", 3 Pgs.

"Japanese Application Serial No. 2004-563613, Office Action mailed Jul. 14, 2010", 2 pgs.

"Japanese Application Serial No. 2004-563613, Response filed Jan. 12, 2011 to Office Action mailed Jul. 14, 2010", 5.

Barbaro, V., et al., "A portable unit for remote monitoring of pacemaker patients", Journal of Telemedicine and Telecare, 3(2), (1997), 96-102.

Bourge, Robert, et al., "Noninvasive Rejection Monitoring of Cardiac Transplants Using High Resolution Intramyocardial Electrograms", PACE, vol. 21, Part II, (Nov. 1998), 2338-2344.

Girouard, Steven D, et al., "Cardiac Rhythm Management Systems and Methods Predicting Congestive Heart Failure Status", U.S. Appl. No. 10/213,268, filed Aug. 6, 2002, 33 pgs.

Hatlestad, John, "Methods and Devices for Detection of Context When Addressing a Medical Condition of a Patient", U.S. Appl. No. 10/269,611, filed Oct. 11, 2002, 29 pgs.

Hutten, H., et al., "Cardiac pacemaker as bridge to cardiac telemonitoring", Biomedizinische Technik, 41(6), Institut for Elektro-und Biomedizinische Technik Technische Universitat Graz., [Article in German With English Abstract], (Jun. 1996), 158-165.

Hutten, H., et al., "Cardiac Telemonitoring through the Linkage of Close-up Telemetry and Internet Transmission", Institute for Electro- and Biomedical Technology, Technical University of Graz Inffeldgasse, 42, [Article in German with English Abstract], (1997), 67-69.

Kenknight, Bruce H, et al., "Method and Apparatus for Establishing Context Among Events and Optimizing Implanted Medical Device Performance", U.S. Appl. No. 10/093,353, filed Mar. 6, 2002, 43 pgs.

Kenknight, Bruce H, "Method and Apparatus for Establishing Context Among Events and Optimizing Implanted Medical Device Performance", U.S. Appl. No. 11/381,051 filed May 1, 2006, 44 pgs.

Kinderman, Michael, et al., "Optimizing the AV Delay in DDD Pacemaker Patients with High Degree AV Block: Mitral Valve Doppler Versus Impedance Cardiography", PACE, vol. 20, (Oct. 1997), 2453-2462.

Leonelli, Fabio M, et al., "Systolic and Diastolic Effects of Variable Atroventricular Delay and Patients with Complete Hear Block and Normal Ventricular Function", Amer. J-Cardiology, vol. 80, (Aug. 1, 1997), 294-298.

Lozier, Luke R, et al., "System for Identifying Candidates for ICD Implantation", U.S. Appl. No. 10/438,261, filed May 14, 2003, 15 pgs.

Ritter, P., et al., "New Method for Determining the Optimal Atrio-Ventricular Delay in Patients Place in DDD Mode for Complete Atrio-Ventricular Block", NASPE Abstracts, (Abstract No. 237), (1995), p. 885.

Zhu, Qingsheng, et al., "Method and Apparatus for Determining Changes in Heart Failure Status", U.S. Appl. No. 10/001,223, filed Nov. 15, 2001, 22 pgs.

US 7,292,140, 11/2007, Mazar et al. (withdrawn)

\* cited by examiner

SYSTEM AND METHOD FOR CORRELATING BIOMETRIC TRENDS WITH A RELATED TEMPORAL EVENT

CROSS REFERENCE TO RELATED APPLICATIONS

This application is a continuation of U.S. application Ser. No. 11/869,611, now issued as U.S. Pat. No. 7,554,438, filed Oct. 9, 2007, which is a continuation of U.S. patent application Ser. No. 10/335,396, now issued as U.S. Pat. No. 7,378,955, filed on Jan. 3, 2003, the specification of which is incorporated herein by reference.

TECHNICAL FIELD

The present device relates generally to a Patient Management System and particularly, but not by way of limitation, to such a system that is adapted to correlate biometric information or trends to a specific temporal event to provide a snapshot of patient health.

BACKGROUND

Management of patients with chronic disease consumes a significant proportion of the total health care expenditure in the United States. Many of these diseases are widely prevalent and have significant annual incidences as well. Heart failure prevalence alone is estimated at over 5.5 million patients in 2000 with incidence rates of over half a million additional patients annually, resulting in a total health care burden in excess of $20 billion. Heart failure, like many other chronic diseases such as asthma, chronic obstructive pulmonary disease ("COPD"), chronic pain, and epilepsy is event driven, where acute episodes of disease result in hospitalization. In addition to causing considerable physical and emotional trauma to the patient and family, event driven hospitalizations consume a majority of the total health care expenditure allocated to the treatment of heart failure.

An interesting fact about the treatment of acute episodes of disease is that hospitalization and treatment occurs after the acute event has happened. However, most Heart Failure patients exhibit prior non-traumatic symptoms, such as steady weight gain, in the weeks or days prior to the acute episode. If the physician is made aware of these symptoms, it is possible to intervene before the event, at substantially less cost to the patient and the health care system.

Intervention before the event is usually in the form of a re-titration the patient's drug cocktail, reinforcement of the patient's compliance with the prescribed drug regimen, or acute changes to the patient's diet and exercise. Such intervention is usually effective in preventing the acute episode and thus avoiding hospitalization. NYHA Class III and late Class II HF patients often have acute episodes three or four times annually, each episode resulting in hospital stays of three or four days.

However, many acute episodes of disease can be predicted by analyzing biometric trends. Predictive accuracy may be improved by analyzing such biometric trends in view of clinically derived algorithms. In practice, the algorithmic analysis of contemporaneous biometric information or data in reference to a temporal event can report and assist in the identification of a state of patient health or disease progression. Yet, data collection and rapid analysis is a limiting factor in effectively using clinical algorithms to report such states of patient health.

Thus, for these and other reasons, there is a need for a system and method for efficiently and effectively reporting a state of patient health or disease progression by correlating biometric information or trends with a related temporal event and alerting the patient or physician of the state of patient health or disease progression.

SUMMARY

According to one aspect of the invention, there is provided a system and method for correlating sensed biometric information or trends using clinically derived algorithms to report a state of patient health. The report of patient health enables a patient or clinician to examine and further analyze a state of health or disease progression in view of a temporal event that may confer additional clinical meaning to or understanding of the reported state of health. The system also may deliver therapy when configured as an implantable medical device.

In one embodiment, the system comprises at least one sensor to sense biometric data, an interactive database, an analysis module to analyze the biometric data, a correlation module to correlate the biometric data with a temporal event, an electronic transmission module to transmit the output to an interactive communications network, a transformation module to transform transmitted output to a recognizable clinical result, and a display module to display the transformed output. By way of non-limiting example only, a temporal event may comprise a change in patient medication, a heart attack, physical injury, dates of personal interest, or other events.

In another embodiment, the interactive communications network comprises a sensor implanted within a patient, a host in communication with the sensor comprising means to input biometric and/or environmental data to an interactive database, an analysis module to analyze biometric data, and a delivery module that communicates the analyzed data in the form of an identified state of patient health via the communications network.

In yet another embodiment, the system comprises a plurality of interactive databases adapted to store historical and patient population data. In this embodiment, the system is adapted to provide therapy to a patient through a specially adapted implantable medical device based on the identified state of patient health. The implantable medical device may also comprise a sensor. The sensor can be internal or external. External sensors may be adapted to record environmental data. The system also may comprise a diagnostic module for diagnosing the performance of the sensor and the interactive communications network.

In a preferred embodiment of the system and method for correlating biometric trends with a related temporal event, the identified state of patient health is made by analyzing biometric data in view of clinically derived algorithms and monitoring the success of previous identifications of a state of patient health. If warranted by the identified state of patient health, the display module displays a configurable alert for action in the form of a clinically relevant graphic or an audible signal.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention, which is set forth in the following claims.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

In the following detailed description, reference is made to the accompanying drawings that form a part hereof, and in which is shown by way of illustration specific embodiments or examples. These embodiments may be combined, other embodiments may be utilized, and structural, logical, and electrical changes may be made without departing from the spirit and scope of the present invention. The following detailed description is, therefore, not to be taken in a limiting sense, and the scope of the present invention is defined by the appended claims and their equivalents.

The present system and method are described with respect to a system and method that is adapted to report a state of patient health by correlating biometric data or trends with a related temporal event. In this way, the system can provide appropriate therapy to a patient in its embodiment as an implantable medical device or provide a clinician with retrospective environmental and/or perceptual data in time coincidence with objective implanted sensor data. The term "biometric" generally refers to the measurement of a living, human characteristic. The term "Advanced Patient Management" refers to the process of creating and collecting patient specific information, storing and collating the information, and generating actionable recommendations to enable the predictive management of patients with chronic disease. The term "temporal event" refers to events in a patient's environment that may or may not cause a health state change. The term "correlation" refers to time coincident events that have been analyzed for causation and health consequence outcome.

Figure 1:
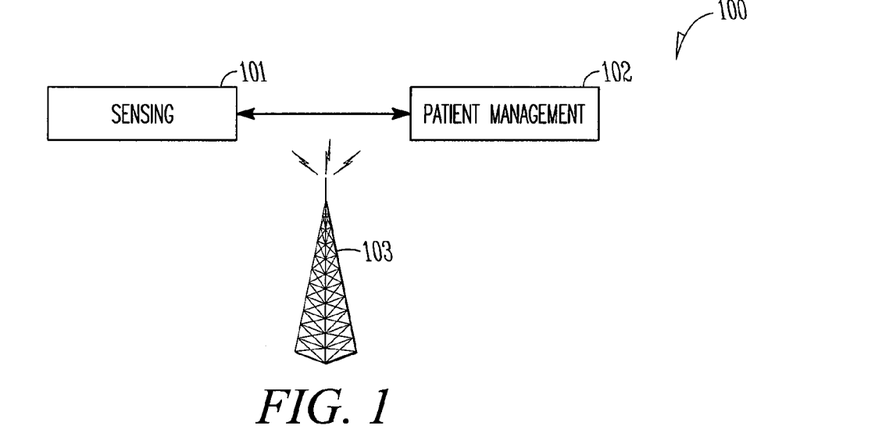
FIG. 1 is a schematic/block diagram illustrating generally, among other things, one embodiment of the system and method for correlating biometric trends with a related temporal event.

FIG. 1 is a schematic/block diagram illustrating generally one embodiment of a system and method for correlating biometric trends with a related temporal event to report a state of patient health. The system 100 further comprises at least one sensor 101 in electronic communication 103 with a patient management system 102 to allow automatic transmission of sensed biometric data to the patient management system 102. Such electronic communication may include wired and/or wireless communication technologies.

Figure 2:
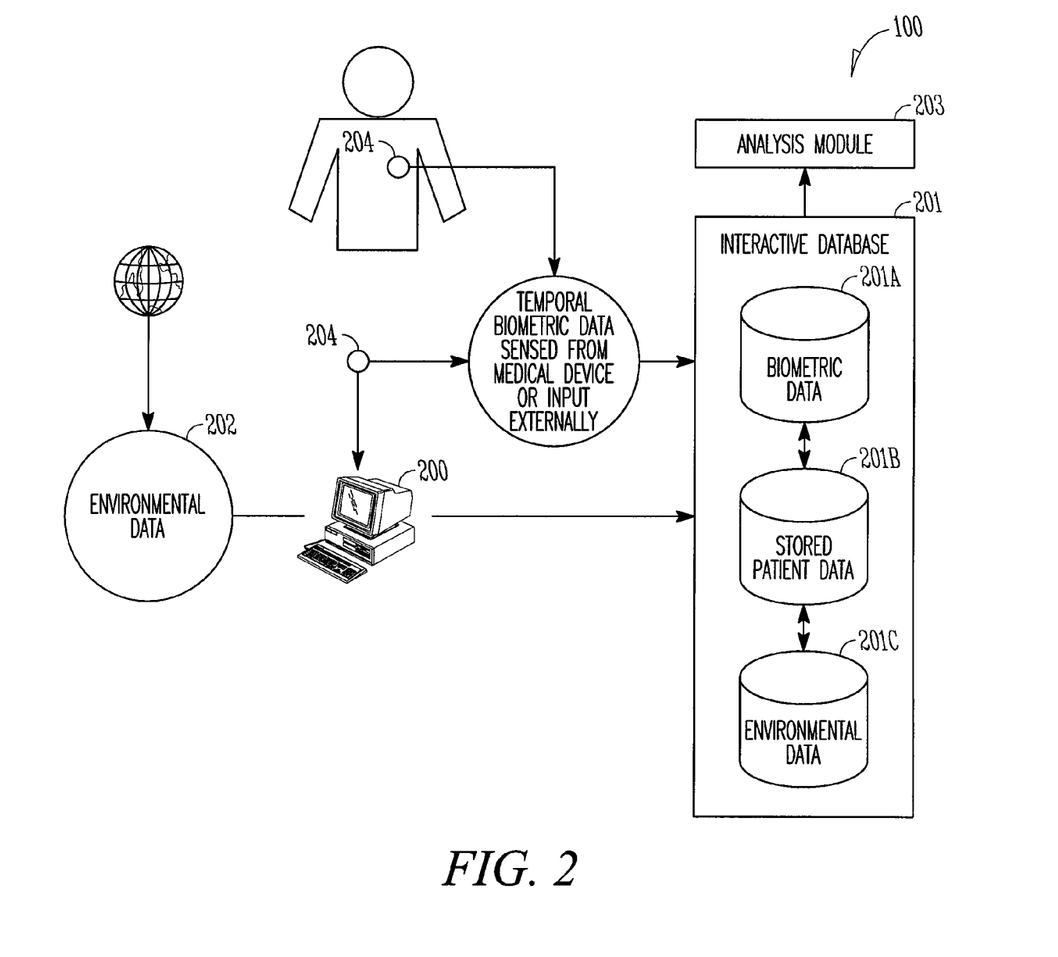
FIG. 2 is a schematic/block diagram illustrating generally, among other things, another embodiment of the system and method for correlating biometric trends with a related temporal event comprising an interactive database and analysis module.

FIG. 2 is a schematic/block diagram illustrating generally another embodiment of the system and method for correlating biometric trends with a related temporal event comprising external means 200 to enter biometric 201a and/or environmental data 202, 201c into at least one interactive database 201 for analysis by an analysis module 203. Environmental data may include temperature, atmospheric pressure, humidity, stress, drug change, diet change, emotional state and/or other objective or subjective data. The database 201 stores data from internal and/or external sensors 204, medical records 201b of a patient, and environmental data 202, 201c. The analysis module 203 identifies a state of patient health based on the information stored in the database 201.

Figure 3:
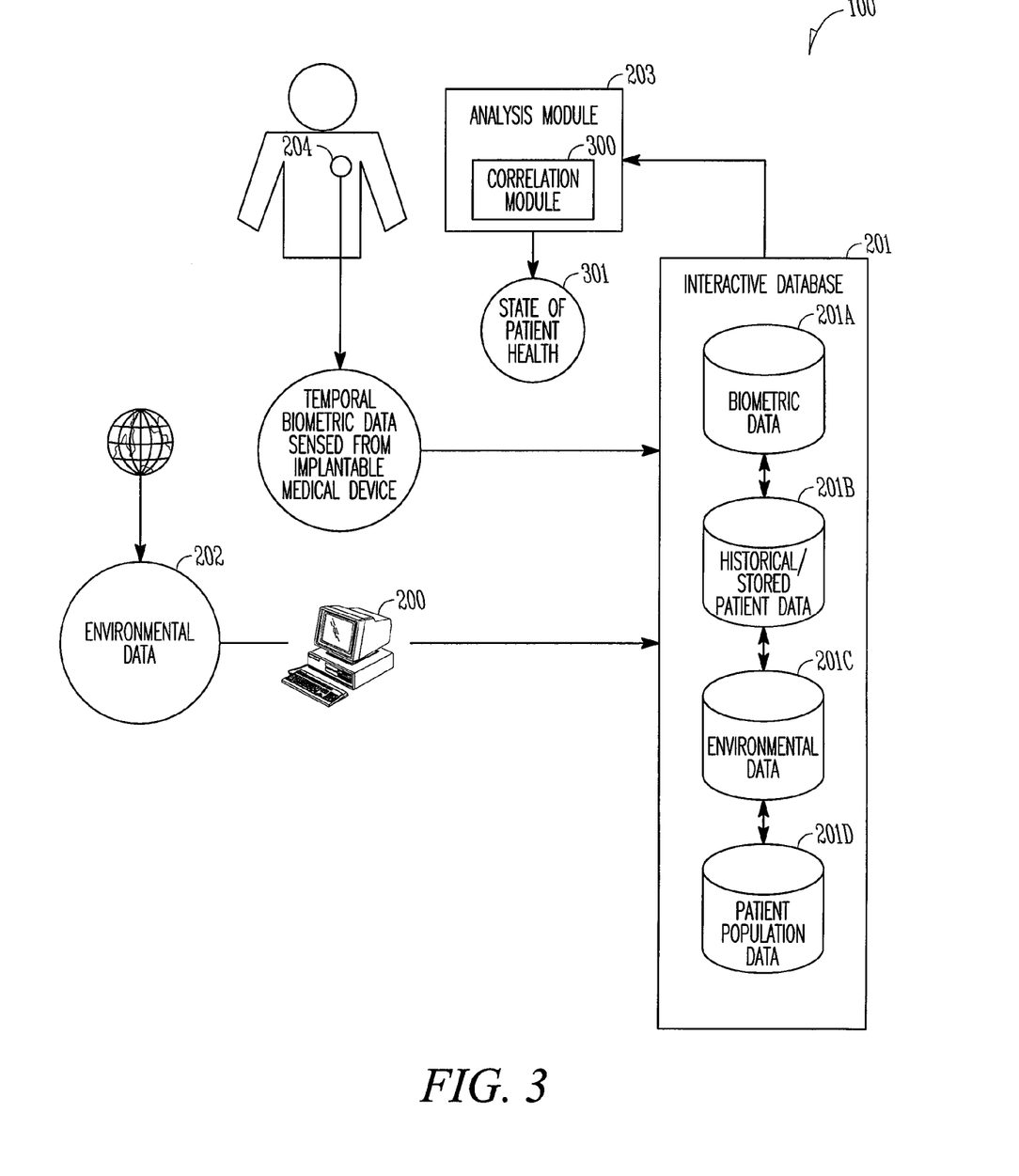
FIG. 3 is a schematic/block diagram illustrating generally, among other things, another embodiment of the system and method for correlating biometric trends with a related temporal event of the present invention comprising a correlation module as a component of an analysis module in electronic communication with an interactive database to report a state of patient health.

FIG. 3 is a schematic/block diagram illustrating generally an embodiment of a correlation module 300 of the system and method for correlating biometric trends with a related temporal event. In addition to at least one internal sensor 204 to sense biometric data and at least one interactive database 201, the system further comprises a correlation module 300 to correlate the biometric data 201a against reference data to create a biometric data set. The reference data may include historical/stored patient data 201b, environmental data 201c and patient population data 201d. Historical patient data may comprise the patient's medical history as manually or electronically entered into the historical/stored patient database 201b. Correlation module 300 may comprise a component of analysis module 203. Biometric 201a and reference data sets 201b, 201c and 201d are transmitted to correlation module 300. Correlation module 300 then correlates the biometric data set with a temporal event to create an output that identifies a state of patient health 301.

Figure 4:
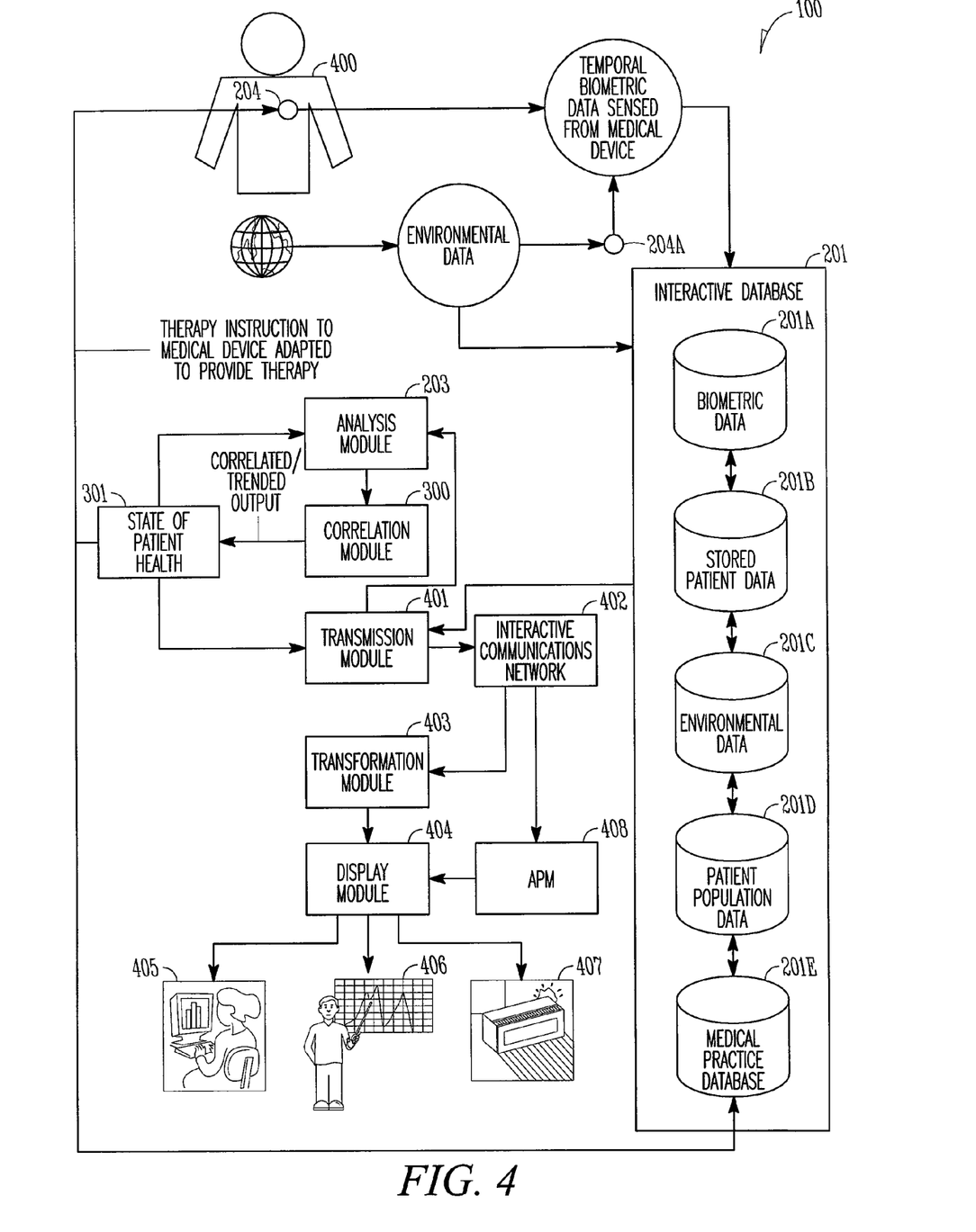
FIG. 4 is a schematic/block diagram illustrating generally, among other things, another embodiment of the system and method for correlating biometric trends with a related temporal event comprising an Advanced Patient Management system in electronic communication with the components of the system.

FIG. 4 is a schematic/block diagram illustrating generally an embodiment of sensors 204 implanted within a patient 400 of the system and method for correlating biometric trends with a related temporal event. The system further comprises an electronic transmission module 401 and an interactive communications network 402. In this embodiment, the correlated output 301 is transmitted via the electronic transmission module 401 to an interactive communications network 402. The output 301 may be transformed by a transformation module 403 and displayed to a clinician or patient 405 via a display module 404 in a human-recognizable format.

In another embodiment as illustrated in FIG. 4, the interactive communications network 402 is in electronic communication with an Advanced Patient Management System ("APM") 408. APM is a system that helps patients, their physicians and their families to better monitor, predict and manage chronic diseases. In the embodiment shown in FIG. 4, the APM system 408 consists of three primary components: 1) an implantable medical device 204 with sensors adapted to monitor temporal biometric data, 2) a Data Management System ("DMS"), which in this embodiment is shown as interactive database 201 and 3) an analytical component 203 adapted to analyze and correlate data from the DMS. APM is designed to support physicians and other clinicians in using a variety of different devices, patient-specific and non-specific data, along with medication therapy, to provide the best possible care to patients. Currently, implanted devices often provide only limited sensing, analysis and therapy to patients. APM moves the device from a reactive mode into a predictive one that allows a clinician to use APM to predict patient health.

In a further embodiment as illustrated in FIG. 4, the interactive database 201 comprises a plurality of interactive databases 201a, 201b, 201c, 201d and 201e. The plurality of interactive databases are adapted to process and store biometric data 201a collected from the sensors, store patient data 201b, environmental data 201c, patient population data 201d and medical practice data 201e. In this embodiment, therapy is provided to a patient via a specially adapted implantable medical device 204 in response to the identified state of patient health 301. A sensor 204a also may be external to a patient 400 to record biometric and environmental data in the database 201.

In a yet another embodiment as illustrated in FIG. 4, the identified state of patient health 301 is based on rules of practicing medicine 201e and revised based on monitoring the success of previous identifications. In this embodiment, the medical practice database 201e comprises clinically derived algorithms of biometric data for automatically reporting a state of patient health 301. The algorithms can be the result of the extraction, codification and use of collected expert knowledge for the analysis or diagnosis of medical conditions. For example, the algorithms can comprise institutional analytical or diagnostic techniques used in specific clinical settings. By reducing the analytical or diagnostic methodologies of institutions like the Cleveland Clinic, the Mayo Clinic or the Kaiser Permanente system to algorithmic expression, a patient will enjoy the benefit of the medical expertise of a leading medical institution without having to visit the institution. The display module 403 is adapted to display a configurable alert for action in the form of a graphical representation 406 of the correlated biometric data and temporal event or an audible signal 407.

It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including," "includes" and "in which" are used as the plain-English equivalents of the respective terms "comprising," "comprises" and "wherein."

What is claimed is:

1. A method comprising:
sensing biometric data using a medical device;
identifying a correlation between the biometric data and an environmental event, wherein the environmental event is capable of causing a health state change in a patient;
transforming the biometric data to produce a transformed output in a human-recognizable format; and
displaying the transformed output and the correlated environmental event in a formatted output.

2. The method of claim 1, wherein sensing biometric data comprises sensing biometric data from an implantable medical device.

3. The method of claim 1, wherein the displaying the biometric data comprises displaying an alert.

4. The method of claim 3, wherein displaying the alert comprises displaying a graphic.

5. The method of claim 3, wherein the alert is configurable.

6. The method of claim 1, wherein the environmental event is selected from a group of events consisting of: a change in temperature, a change in atmospheric pressure, a change in humidity, a change in stress, a change in patient medication, a change in patient diet, and a change in patient emotional state.

7. The method of claim 1, comprising:
obtaining reference data from a database comprising one or more of historical patient data, environmental data, and patient population data;
identifying a correlation between the reference data and the biometric data to obtain a correlated output;
transforming the correlated output to a human-recognizable format; and
displaying the correlated output in the human-recognizable format.

8. The method of claim 1, wherein the transformed output indicates a state of patient health, and comprising providing a therapy in response to the state of patient health.

9. The method of claim 8, wherein providing the therapy comprises:
providing the therapy via the medical device.

10. The method of claim 9, wherein providing the therapy via the medical device comprises:
providing the therapy via an implantable medical device.

11. A system, comprising:
a sensor coupled to a medical device configured to sense biometric data;
a correlation module configured to correlate the biometric data with an environmental event to create a correlated output, wherein the environmental event is capable of causing a health state change in a patient;
a transformation module configured to transform the correlated output to a human-recognizable format; and
a display module configured to display the transformed output, wherein the transformed output comprises the biometric data displayed with the corresponding environmental event.

12. The system of claim 11, wherein the medical device is an implantable medical device.

13. The system of claim 11, wherein the display module is configured to display an alert.

14. The system of claim 13, wherein the alert is configurable.

15. The system of claim 11, wherein the environmental event is selected from a group of events consisting of: a change in temperature, a change in atmospheric pressure, a change in humidity, a change in stress, a change in patient medication, a change in patient diet, and a change in patient emotional state.

16. The system of claim 11, comprising:
an analysis module to analyze the biometric data against a reference data set to create a biometric data set,
and wherein the correlation module is configured to identifying a correlation between reference data and the biometric data to obtain a correlated output,
and wherein the transformation module is configured to transform the correlated output to a human-recognizable format,
and wherein the display module is configured to display the correlated output in the human-recognizable format.

17. The system of claim 11, wherein the transformed output indicates a state of patient health, and comprising a therapy module configured to provide a therapy in response to the state of patient health.

18. The system of claim 11, wherein the therapy module incorporated into the medical device.

19. A system comprising:

a medical device;

means for sensing biometric data using the medical device;

means for identifying a correlation between the biometric data and an environmental event, wherein the environmental event is capable of causing a health state change in a patient;

means for transforming the biometric data to produce a transformed output in a human-recognizable format; and means for displaying the transformed output and the correlated environmental event in a formatted output.

* * * * *